(12) United States Patent
Brewer et al.

(10) Patent No.: US 10,335,563 B2
(45) Date of Patent: Jul. 2, 2019

(54) ACTUATOR FOR AN INHALER

(71) Applicant: 3M INNOVATIVE PROPERTIES COMPANY, St. Paul, MN (US)

(72) Inventors: Richard D Brewer, Loughborough (GB); Adam J Stuart, Loughborough (GB); Neale F Griffiths, Aylesbury (GB)

(73) Assignee: 3M Innovative Properties Company, St. Paul, MN (US)

( * ) Notice: Subject to any disclaimer, the term of this patent is extended or adjusted under 35 U.S.C. 154(b) by 854 days.

(21) Appl. No.: 14/890,495

(22) PCT Filed: May 12, 2014

(86) PCT No.: PCT/US2014/037649
§ 371 (c)(1),
(2) Date: Nov. 11, 2015

(87) PCT Pub. No.: WO2014/186263
PCT Pub. Date: Nov. 20, 2014

(65) Prior Publication Data
US 2016/0121060 A1     May 5, 2016

(30) Foreign Application Priority Data
May 14, 2013   (GB) .................................. 1308679.8

(51) Int. Cl.
*A61M 15/00* (2006.01)
*A61M 15/08* (2006.01)

(52) U.S. Cl.
CPC ...... *A61M 15/009* (2013.01); *A61M 15/0025* (2014.02); *A61M 15/0026* (2014.02);
(Continued)

(58) Field of Classification Search
CPC ............ A61M 15/009; A61M 15/0021; A61M 15/0025; A61M 15/0026; A61M 15/0071; A61M 11/08
(Continued)

(56) References Cited

U.S. PATENT DOCUMENTS 2,914,222 A   11/1959   Meshberg
3,001,524 A   9/1961    Maison
(Continued)

FOREIGN PATENT DOCUMENTS

EP      0132352      1/1985
EP      0703159      3/1996
(Continued)

OTHER PUBLICATIONS

International Search Report for PCT International Application No. PCT/US14/37649 dated Dec. 8, 2014, 4 pages.
Ext_EP_Search_Report_EP14797022.2 dated Dec. 16, 2016.

*Primary Examiner* — Colin W Stuart
*Assistant Examiner* — Douglas Y Sul

(57) ABSTRACT

An actuator for an inhaler, in particular a nasal actuator, is disclosed, the actuator comprising a body, a stem post and fixing means for fixing the stem post in the body. The body comprises a delivery passage for delivery of a medicament and a canister opening for insertion of a canister having a metering valve with a valve stem. The stem post comprises a stem socket for receiving the valve stem of a canister and comprises an orifice for discharging a medicament to the delivery passage. The stem post and body are adapted so they cooperate to define a transition chamber when the stem post is fixed in the body. Also disclosed is a method of forming an component for an actuator for an inhaler, and a
(Continued)

method of assembling an actuator for an inhaler by inserting the stem post through the canister opening and into the body thereby.

17 Claims, 8 Drawing Sheets

(52) U.S. Cl.
CPC ..... *A61M 15/0071* (2014.02); *A61M 15/0075* (2014.02); *A61M 15/08* (2013.01); *A61M 2207/00* (2013.01)

(58) Field of Classification Search
USPC .................................................. 128/200.23
See application file for complete search history.

(56) References Cited

U.S. PATENT DOCUMENTS

| | | | |
|---|---|---|---|
| 3,320,952 A | 5/1967 | Wright | |
| 3,361,306 A | 1/1968 | Grim | |
| 3,865,279 A | 2/1975 | James | |
| 3,913,842 A | 10/1975 | Singer | |
| 4,969,578 A | 11/1990 | Gander | |
| 5,115,803 A | 5/1992 | Sioutas | |
| 5,119,806 A | 6/1992 | Palson | |
| 6,615,826 B1 | 9/2003 | Gabrio | |
| 6,640,805 B2 | 11/2003 | Castro | |
| 2003/0015191 A1* | 1/2003 | Armstrong | A61M 15/0028 128/200.21 |
| 2003/0089368 A1 | 5/2003 | Zhao | |
| 2004/0255936 A1* | 12/2004 | Urbanus | A61M 15/009 128/200.23 |
| 2006/0076010 A1* | 4/2006 | King | A61M 15/0045 128/200.23 |
| 2007/0017506 A1 | 1/2007 | Bell | |
| 2009/0159081 A1 | 6/2009 | Stadelhofer | |
| 2010/0224185 A1* | 9/2010 | Anderson | A61M 15/009 128/200.23 |
| 2011/0155129 A1 | 6/2011 | Stedman | |
| 2012/0085345 A1* | 4/2012 | Zeng | A61M 15/009 128/200.23 |
| 2013/0087142 A1* | 4/2013 | Kane | A61M 15/009 128/200.23 |
| 2015/0122257 A1* | 5/2015 | Winkler | A61M 11/02 128/203.15 |

FOREIGN PATENT DOCUMENTS

| | | |
|---|---|---|
| FR | 2831841 | 5/2003 |
| GB | 868785 | 5/1961 |
| GB | 1021739 | 3/1966 |
| GB | 1219090 | 1/1971 |
| GB | 1506118 | 4/1978 |
| GB | 2143283 | 2/1985 |
| GB | 2170430 | 8/1986 |
| GB | 2196262 | 4/1988 |
| GB | 2312379 | 10/1997 |
| GB | 2366519 | 3/2002 |
| GB | 2415388 | 12/2005 |
| WO | WO 1998-31411 | 7/1998 |
| WO | WO 1998-51360 | 11/1998 |
| WO | WO 1999-01229 | 1/1999 |
| WO | WO 1999-24506 | 5/1999 |
| WO | WO 1999-25407 | 5/1999 |
| WO | WO 2000-01436 | 1/2000 |
| WO | WO 2000-50112 | 8/2000 |
| WO | WO 2000-76567 | 12/2000 |
| WO | WO 2001-36033 | 5/2001 |
| WO | WO 2002-096490 | 12/2002 |
| WO | WO 2004-094068 | 11/2004 |
| WO | WO 2005-120617 | 12/2005 |
| WO | WO 2008-023015 | 2/2008 |
| WO | WO 2008-023018 | 2/2008 |
| WO | WO 2008-024728 | 2/2008 |
| WO | WO 2011-133744 | 10/2011 |

* cited by examiner

ACTUATOR FOR AN INHALER

CROSS REFERENCE TO RELATED APPLICATIONS

This application is a national stage filing under 35 U.S.C. 371 of PCT/US2014/037649, filed May 12, 2014, which claims priority to United Kingdom Patent Application No. 1308679.8, filed May 14, 2013, the disclosure of which is incorporated herein by reference in its/their entirety herein.

FIELD OF THE INVENTION

The present invention relates to actuators for metered dose inhalers, to metered dose inhalers, to methods for producing actuators for such inhalers and to methods of assembling inhalers.

BACKGROUND OF THE INVENTION

Pressurized metered dose inhalers (pMDI) may be used for delivering medication in the form of aerosols to patients. The route of delivery of the medicament using such inhalers may be oral or nasal.

Such an inhaler commonly comprises a canister containing the medicament aerosol formulation, and an actuator with a delivery passage. The canister contains the aerosol formulation, either as a solution or suspension, in the form of one or more drugs and propellant, and optionally excipients, selected from co-solvents, surfactants, stabilizing substances (for chemical or physical stability) and flavourings. The canister also comprises a metering valve arranged to deliver a metered dose of the medicament on actuation of the inhaler.

The actuator typically comprises a housing, generally made of a plastic material, within which the canister is located. A portion of the canister will usually project above the actuator housing.

In oral inhalers the actuator has a delivery passage in the form of a mouthpiece that is placed in the patient's mouth and through which the medicament passes on being dispensed. The patient places the mouthpiece in their mouth and breathes in, creating an air flow from the actuator through the mouthpiece and into the mouth and lungs. At the same time the patient actuates dispensation of the medicament from the canister. Actuation may occur as a result of inhalation by the patient or the patient may manually actuate the inhaler, for example, by depressing the projecting portion of the canister further into the housing. Nasal actuators operate in a similar fashion, but instead of a mouthpiece the actuator is provided with a nosepiece for delivery of the medicament to the nasal passages. In the case of nasal medicament delivery, there is not a need for the concurrent inhalation of air, however.

WO-A-98/031411 discloses an aerosol inhalation device that is manually operated and comprises a holding part for receiving an aerosol container with a valve and outlet tip, an inspiratory part and a member for passage of aerosol.

US-A-2003/0089368 discloses nozzles for aerosol propellant systems, and more particularly aerosolization spray nozzles for metered dose inhalers.

U.S. Pat. No. 3,361,306 discloses an aerosol device for dispensing a liquid containing a medically active ingredient dissolved or suspended therein.

WO-A-99/25407 discloses an actuator for an inhaler for administering medicament by inhalation.

GB-A-2,143,283 discloses applicators for dispensing medicaments from a pressurised dispensing container.

GB-A-2,170,430 is concerned with improvements relating to spray nozzles, particularly of the kind that are used to dispense a fine spray of liquid.

GB-A-1,021,739 relates to a device for use in inhalation therapy with aerosols.

GB-A-2,366,519 discloses a dispensing apparatus for use with pressurised dispensing containers and, in particular, an apparatus for dispensing orally inhaled medicinal products in aerosol form.

SUMMARY OF THE INVENTION

Known actuators do not, however, take account of the need to accommodate various designs of canister valve. Actuators in the documents listed above do not take account of the need to provide devices to improve the assurance for patients in their use of inhalers, for example, dose indicators. Furthermore, it may be complex and costly to manufacture actuators to the required tolerances and quality.

In a first aspect, the present invention accordingly provides an actuator for an inhaler, the actuator comprising a body (preferably an elongate body), a stem post and fixing means for fixing the stem post in the body, wherein the body comprises a delivery passage for delivery of a medicament and a canister opening for insertion of a canister having a metering valve with a valve stem, the stem post comprises a stem socket for receiving the valve stem of a canister and comprises an orifice for discharging a medicament to the delivery passage, and wherein the stem post is adapted and the body is adapted so that the stem post and body cooperate to define a transition chamber when the stem post is fixed in the body.

Arranging the stem post and body to define a transition chamber is advantageous because it facilitates manufacture of an actuator with a relatively longer orifice and/or with a relatively longer, optional, expansion chamber. The possibility of having a longer orifice allows selection of appropriate characteristics of the spray exiting from the orifice. It is important to optimise the spray characteristics for medicament delivery, and for patient comfort particularly in nasal drug delivery applications. The longer, optional, expansion chamber allows more space to incorporate other components in the actuator (e.g. a dose counter). The longer orifice and/or the longer, optional, expansion chamber are of particular benefit when the spray is directed at an upward angle for intranasal administration.

Generally, the transition chamber may be situated between the stem socket and the delivery passage, preferably between the stem socket and the orifice. Thus, the transition chamber is preferably in fluid communication with the stem socket and the delivery passage. The transition chamber is preferably in fluid communication between the stem socket and the orifice.

Preferably, the orifice and the expansion chamber are the only communicating ports in the transition chamber.

Preferably, the fixing means are adapted so that the stem post is fixable in the body by insertion of the stem post through the canister opening. This is advantageous, because it has surprisingly been found that when the actuator is provided with fixing means that enable the stem post component to be fixed by insertion through the canister opening, this assists in the formation of a good seal between the actuator body component and the actuator stem post component. Such a seal may be further improved as the patient depresses the canister. Surprisingly, alignment of the orifice with the delivery passage is also much improved.

The stem post may be adapted to be fixable solely by the action of insertion. In some embodiments additional fixing means such as clips, adhesives and/or welding portions may also be used to fix the stem post and the body. Welding may be heat, ultrasonic and/or laser welding.

Preferably, intake of air for patient inhalation is provided through the canister opening.

Preferably, the stem post comprises a first transition region, preferably situated between the stem socket and the orifice.

Preferably, the stem post further comprises an expansion chamber for receiving at least a portion of a metered dose of the medicament from the canister. Usually, the expansion chamber will be situated between the stem socket and first transition region and is preferably in fluid communication with the stem socket and first transition region.

Preferably, the body comprises a second transition region. It is preferred if the second transition region comprises a transition recess. More preferably the second transition region or transition recess is situated in a post seat extending upwardly from the base of the body. The stem post and body are preferably adapted so that the first transition region forms part of the transition chamber when the stem post is fixed to the body and/or the second transition region (e.g. the transition recess) forms part of the transition chamber when the stem post is fixed to the body.

Thus, in a preferred embodiment, the first transition region and the second transition region define (preferably cooperate to define) the transition chamber when the stem post is fixed in the body.

The orifice, preferably, comprises a jet portion of predetermined width and predetermined length, that preferably extends from the transition chamber to the orifice outlet. The predetermined width may be in the range 0.1 mm to 1.5 mm. The predetermined length may be in the range 0.05 mm to 5 mm, preferably 0.4 mm to 3 mm. The orifice may be generally of any cross sectional shape (e.g. oval, rectangular) but is preferably generally circular.

The fixing means preferably comprises at least one press fit seal which may be a ring and groove press fit seal. Typically, the ring portion of a ring and groove press fit seal will be on the stem post, with the groove situated in the actuator body. However, the ring may alternatively be on the body with the groove on the stem post. The press fit seal preferably forms an interference fit seal when engaged.

The fixing means may comprise an adhesive portion (where an adhesive has been used to fix the stem post and body) and/or a welded portion (where a welding process has been used to fix the stem post and body). The welded portion may be an ultrasonic, laser and/or heat welded portion.

The fixing means may additionally comprise at least one clip.

The fixing means is preferably tamper-proof, or advantageously at least tamper-evident to discourage a patient from separating the stem post from the actuator body.

Preferably, the body and/or stem post may further comprise alignment features, for example asymmetric lugs, keying features, cradles, clips or flat surfaces that in combination with other alignment features define a position of alignment and engagement.

The stem post may be a unitary moulding (i.e. the stem post may be or is produced by moulding in one piece). This is particularly advantageous because it leads to manufacturing efficiency. Previously, it has been difficult to consistently mould an actuator in one piece, at least partly because of the need for tight tolerances and particularly minimal moulding flash. This has previously been a particular problem in the case of nasal inhalers where there is an acute angle between the stem socket/expansion chamber and delivery passage of the actuator. In the present invention, this problem is addressed by the use of a separate but fixable stem post (usually of a smaller size than the assembled actuator), which enables higher tolerances to be achieved in the mould with a significant reduction in flash. A further benefit of the actuator of the present invention is that the stem socket may be adapted to receive a particular design of valve and/or design of valve stem. Thus, whereas in known actuators the whole actuator would have to be re-designed to accommodate a different design of valve, in the present specification a much smaller piece is required to be moulded to take account of a differing design. Little or no change need usually be made to the body, with advantages in manufacturing efficiency and inventory control and reduction in tooling cost.

It is advantageous if the body is a unitary moulding (i.e. the body may be or is produced by moulding in one piece).

In a preferred embodiment, the actuator may be a nasal actuator. Consequently, the delivery passage may comprise a nose piece adapted for nasal delivery of the medicament. The nosepiece is preferably angled upwardly at an acute angle with respect to the long axis of the body, preferably at 85° or less, more preferably at 75° or less or 70° or less, most preferably at about 66°.

The body may further comprise a window, preferably an indicator viewing window. The indicator viewing window is particularly useful for display of a dose indication or a dose count if the actuator further comprises a dose indicator or a dose counter.

Thus, preferably, the stem post further comprises supporting means (i.e. first supporting means) for supporting a dose indicator or a dose counter. Such supporting means may be, for example wing portions on the stem post. The body may alternatively or additionally comprise second supporting means for supporting a dose indicator or dose counter.

In a second aspect, there is provided an inhaler comprising an actuator as discussed in relation to the first aspect or the second aspect, and a canister.

The actuator may be produced by moulding, preferably injection moulding.

Thus, in a third aspect, there is provided a method of forming an insertable component for an actuator for an inhaler, the method comprising providing a mould for moulding the component, the mould comprising a transition feature (preferably a male transition feature) and at least two moulding pins, arranging the moulding pins so that an end of each moulding pin is in contact with a surface of the transition feature, and injecting at least a first polymer into mould (preferably into the mould cavity of the mould).

Preferably, the two moulding pins comprise a first moulding pin for forming the expansion chamber of the component and a second moulding pin for forming the orifice of the component. The transition feature provides for the formation of the first transition region. The transition feature will usually have at least a first surface and a second surface, and the first moulding pin will usually be arranged to contact the first surface and the second moulding pin will be arranged to contact the second surface. The angle subtended by the two moulding pins when they are in contact with the respective surfaces of the transition feature is preferably acute, preferably at 85° or less, more preferably at 75° or less or 70° or less, most preferably at about 66°.

Preferably, the ends of the pins are adapted to contact flush with the transition feature and meet it transversely (preferably substantially orthogonally) during moulding. Preferably the ends of the pins are flat. This transverse (preferably substantially orthogonal) contact limits lateral forces on the pins, allowing longer pins to be used without risk of flash on the moulded item.

This aspect is especially advantageous because it enables the use of relatively long and thin moulding pins, e.g. to form an appropriately dimensioned expansion chamber and an appropriately dimensioned orifice. Previously, attempts to make actuators using long, thin pins have sometimes resulted in flash which may require subsequent processing to remove.

In a fourth aspect the present invention provides a method of assembling an actuator for an inhaler, the method comprising providing a body, a stem post and fixing means for fixing the stem post in the body, wherein the body comprises a second transition region, a delivery passage for delivery of a medicament and a canister opening for insertion of a canister having a metering valve with a valve stem, and wherein the stem post comprises a first transition region, a stem socket for receiving the valve stem of a canister, and an orifice for discharging a medicament to the delivery passage, and inserting the stem post through the canister opening into the body thereby fixing the stem post in the body and wherein the first transition region and the second transition region define (i.e. cooperate to define) the transition chamber when the stem post is fixed in the body.

Throughout this specification, the word "inhaler" means a device for delivery of a medicament in fluid (or powder) form either orally or nasally and does not imply that the device requires inhalation on the part of the patient during delivery. It is known that a medicament may be delivered successfully to the nasal passages by an inhaler without the need for the patient to inhale.

BRIEF DESCRIPTION OF THE DRAWINGS

So that the present specification may be more completely understood, reference is made, by way of example only, to the accompanying drawings in which.

In the drawings, like reference numerals are used to refer to like parts.

DETAILED DESCRIPTION

Figure 1:
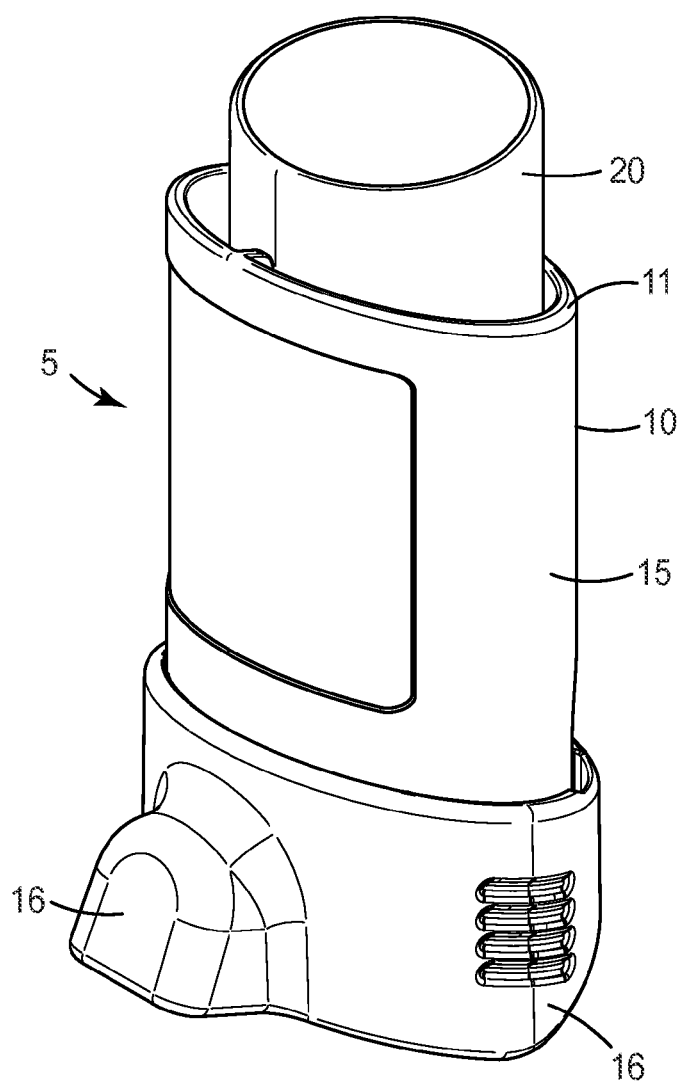
FIG. 1 is a perspective front view of an embodiment of an inhaler.

FIG. 1 illustrates, in perspective view, a pressurised metered dose inhaler 5 comprising a canister 20 and an actuator 10. The canister 20 is pressurised and holds medicament for delivery via the actuator 10. The actuator 10 has a generally elongate actuator body 15 that acts as a housing for the canister 20. The canister 20 is inserted into the canister opening 11 at the top portion of the actuator 10. The inhaler 5 is a nasal inhaler, having a nose piece (see FIG. 4) covered by a cap 16.

Figure 2:
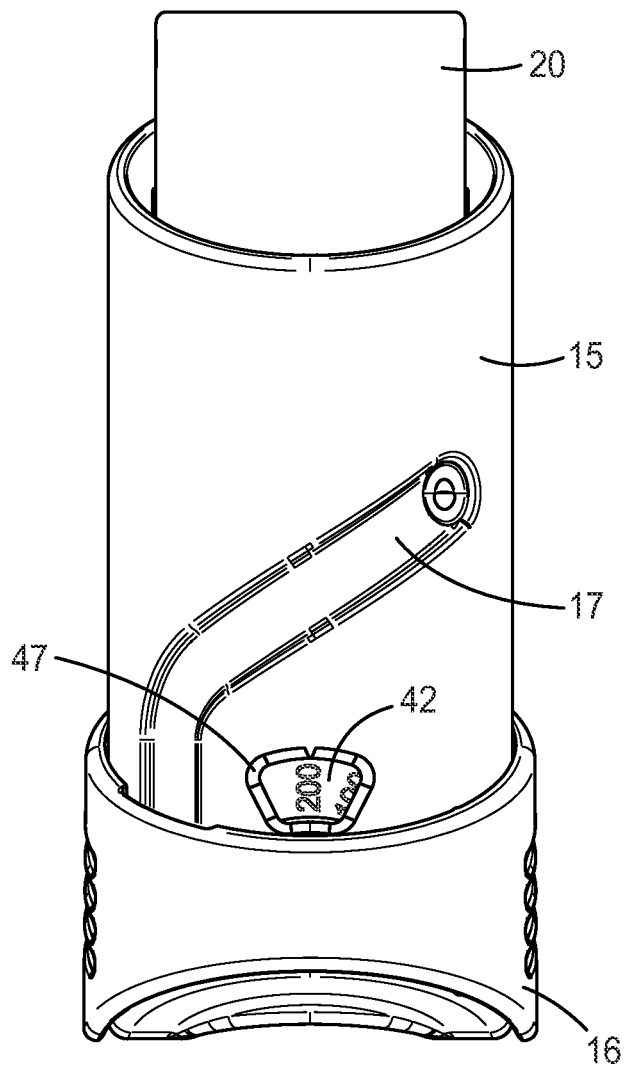
FIG. 2 is a rear view of the inhaler of FIG. 1.

FIG. 2 shows, in a rear view, the actuator body 15, the actuator cap 16, and the canister 20. The body 15 has a cap track 17 arranged to guide the cap 16 from a closed position in which the cap 16 covers the nose piece (the position as shown in FIGS. 1 and 2) to an open position (not shown) in which the nose piece 30 is uncovered. The body 15 has a viewing window 47 through which the display of a dose indicator 42 is visible.

Figure 3:
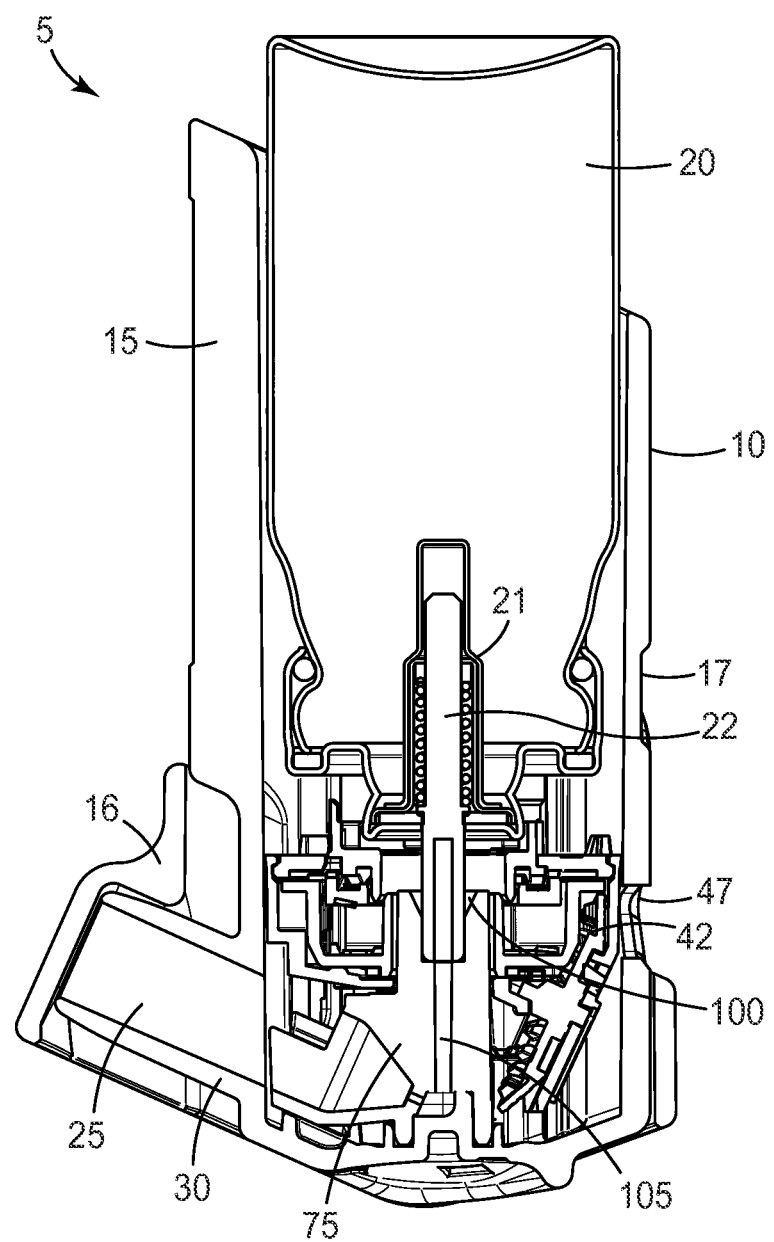
FIG. 3 illustrates a vertical section through the inhaler of FIG. 1 and FIG. 2.

FIG. 3 shows a vertical section through the inhaler 5. The actuator 10 comprises the body 15 and a separate unitary moulded stem post 75. The stem post 75 is fixed in the body 15 and the stem post 75 has a stem socket 100 for receiving the canister valve stem 22 of the canister metering valve 21. In use, the patient would displace cap 16 from the nose piece 30, insert the nose piece 30 into a nostril and exert pressure on the top of the canister 20. This moves the canister 20 into the body 15 of the actuator and presses the canister valve stem 22 against the stem post 75, resulting in the canister metering valve 21 opening and releasing a metered dose of medicament into an expansion chamber 105 within the stem post 75. The expansion chamber 105 is in fluid communication with a delivery passage 25 in the body 15 so the medicament is delivered through the delivery passage 25 and out of the nose piece 30 into the patient's nostril. A dose indicator 42 is situated at the lower rear portion of the body 15 so that its indicia are visible through the indicator window 47. The dose indicator 42 is so arranged that movement of the canister 20 in use indexes the dose indicator 42.

Figure 4:
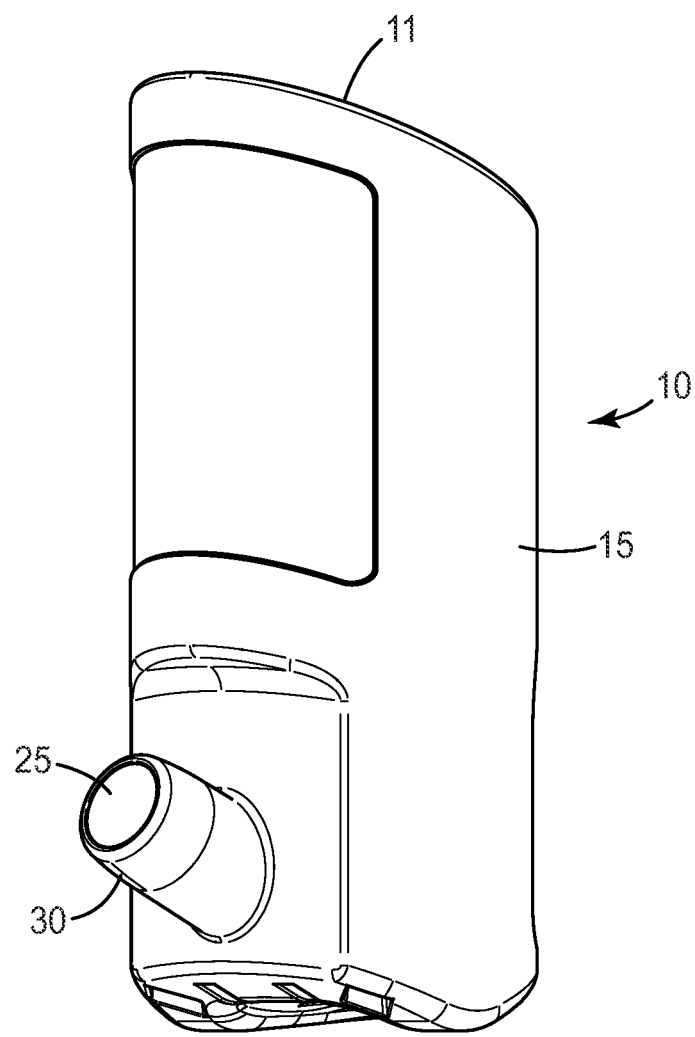
FIG. 4 is a perspective view of the actuator of the inhaler of FIGS. 1 to 3.

FIG. 4 shows the actuator 10 with the cap 16 and canister 20 removed. The nose piece 30 is angled upwardly at an acute angle with respect to the long axis of the body 15 for convenient insertion into the nostril of a patient. The nose piece 30 has a delivery passage 25 through which the medicament is delivered.

Figure 5:
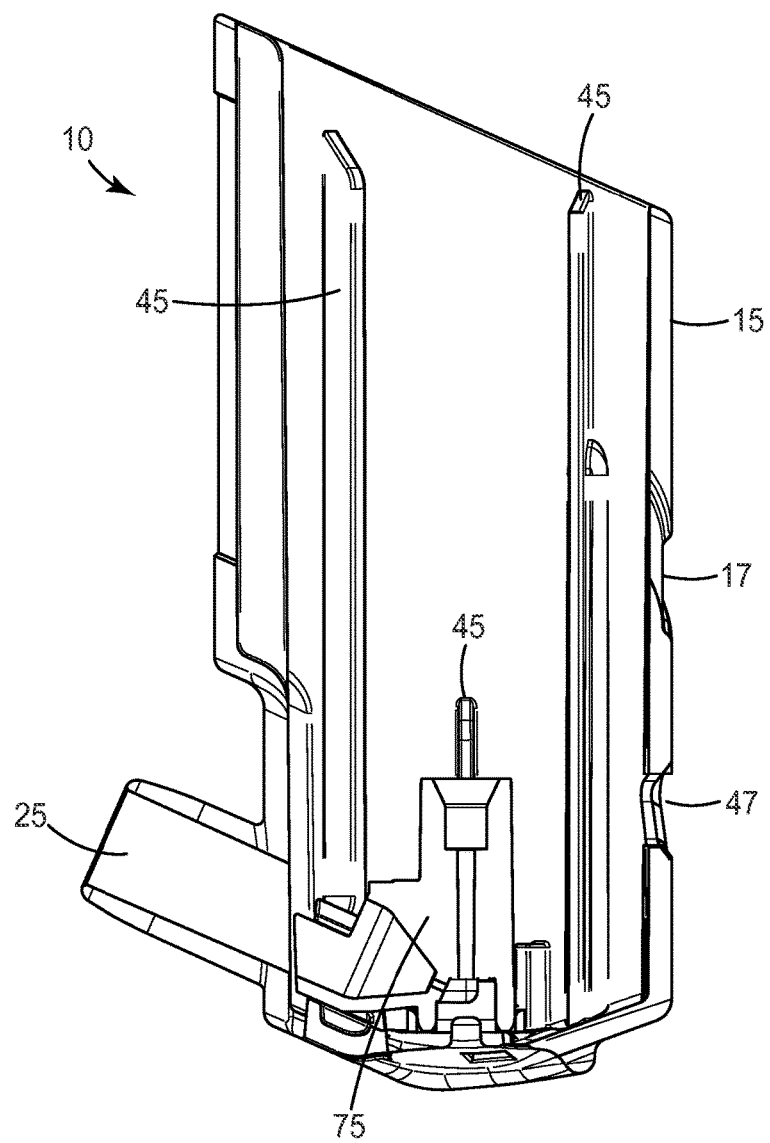
FIG. 5 is a vertical section through the actuator of FIG. 4.
Figure 6:
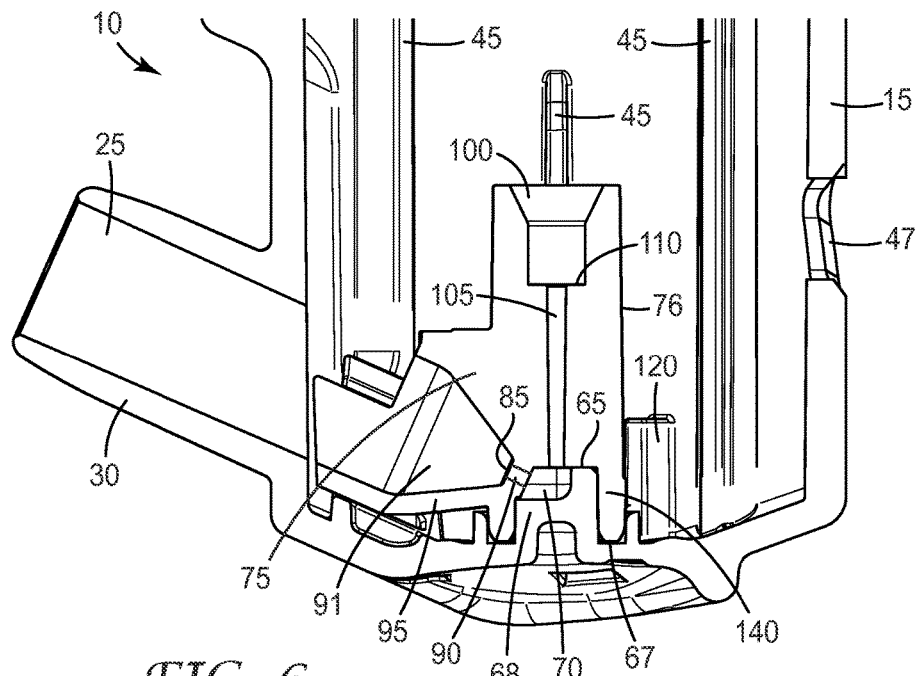
FIG. 6 is a magnified view corresponding to the lower portion of FIG. 5.

FIG. 5 shows a vertical section through an actuator 10 as illustrated in FIG. 4. FIG. 6 shows a section through the lower portion of the actuator 10. In both FIGS. 5 and 6 the dose indicator 42 (shown in FIG. 3) is not present; otherwise the features of the actuator 10 are as shown in FIG. 3. FIG. 5 also shows ribs 45 that locate the canister 20 in the correct position in the body 15 of the actuator 10.

The delivery passage 25 in the nose piece 30 is arranged to receive doses of medicament through a stem post delivery passage 91, partly defined by the spray cone 95 of the stem post 75. The stem post 75 is a separate moulding fixed in the body 15 with a press fit sealing ring 140 in press fit sealing groove 67 of the body 15. The stem post delivery passage 91 is in fluid communication with an orifice outlet 85 in the stem post 75. The orifice outlet 85 is in fluid communication through a jet portion 90 with a transition chamber 70. The jet portion 90 is of predetermined width and predetermined length and may be in the form of a cylindrical tube of diameter 0.1 to 1.5 mm and of length 0.05 to 5 mm, the length usually being 0.4 mm to 3 mm. The transition chamber 70 is formed by parts of both the body 15 and the stem post 75, in particular, by a body transition region formed by the configuration of a post support 68 and post seat 65 together with the transition region 77 (not shown in FIG. 6; see FIGS. 8 and 10) of the stem post 75.

In use, a metered dose of medicament is delivered from the valve 21 of the canister 20 (not shown in FIG. 6) through the expansion chamber 105 of the stem post 75, into the transition chamber 70 formed by the interaction/cooperation of the stem post transition region 77 and a body transition region (including transition recess 64) (see FIG. 11) in the post support 68 of the body 15, and out of the orifice outlet 85 via the jet portion 90. From the orifice outlet 85, the dose is delivered through the spray cone 95, the stem post delivery passage 91 and the delivery passage 25.

Figure 7:
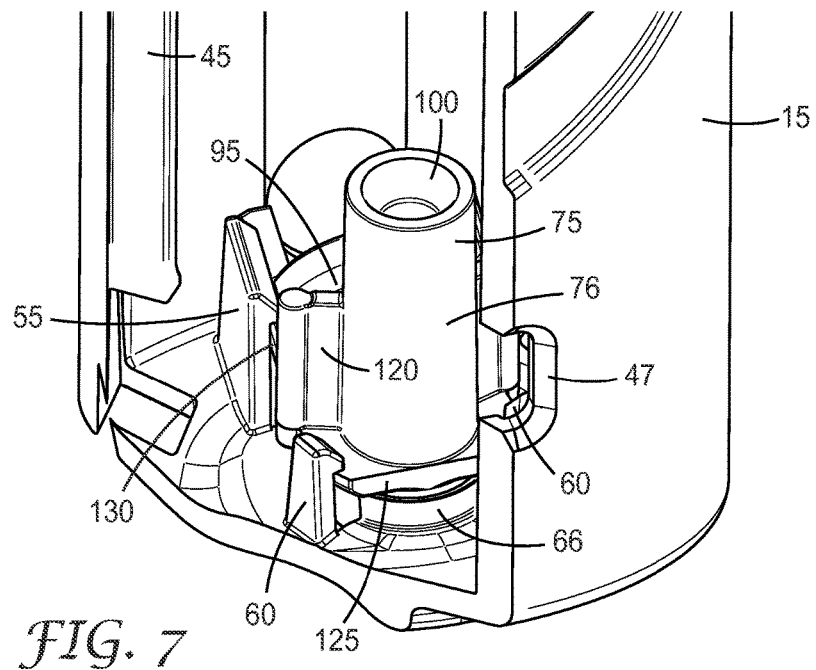
FIG. 7 is a partial rear perspective cut-away view of the actuator of FIG. 4.

As shown in FIG. 7, the stem post 75 is additionally fixed in position in the body 15 through clips 55, 60 cooperating respectively with a cone edge 130 on the stem post and a post flange 125 on the stem post 75.

The stem post 75 has wings 120 to support a dose indicator 42 (not shown in FIG. 7) in the body 15, such that a display of the dose number is visible through the indicator viewing window 47.

Ribs 45 on the body 15 locate the canister (not shown in FIG. 7) when inserted in the body 15. The stem socket 100 accepts the valve stem 22 of the canister 20 and the valve 21 is supported on a stem ledge 110 (shown in FIG. 6). The stem post 75 has an elongate tube portion 76.

The cone clips 55 cooperate with the cone edge 130 and the post clips 60 cooperate with the post flange 125 to help fix the stem post 75 in the body 15. A sealing rim 66 forming the outer part of the press fit seal provides a sealing fit of the stem post 75 in the body 15.

Figure 8:
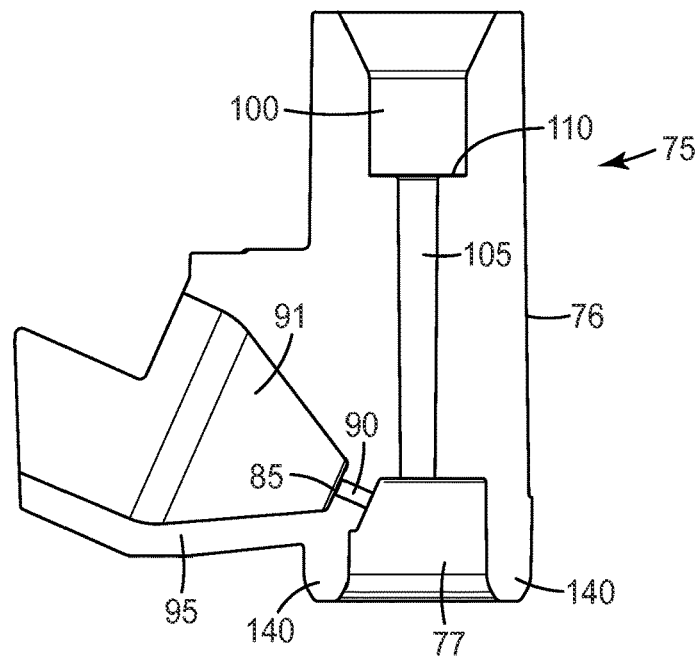
FIG. 8 is a vertical section through the stem post of the inhaler of FIGS. 1 to 3.
Figure 9:
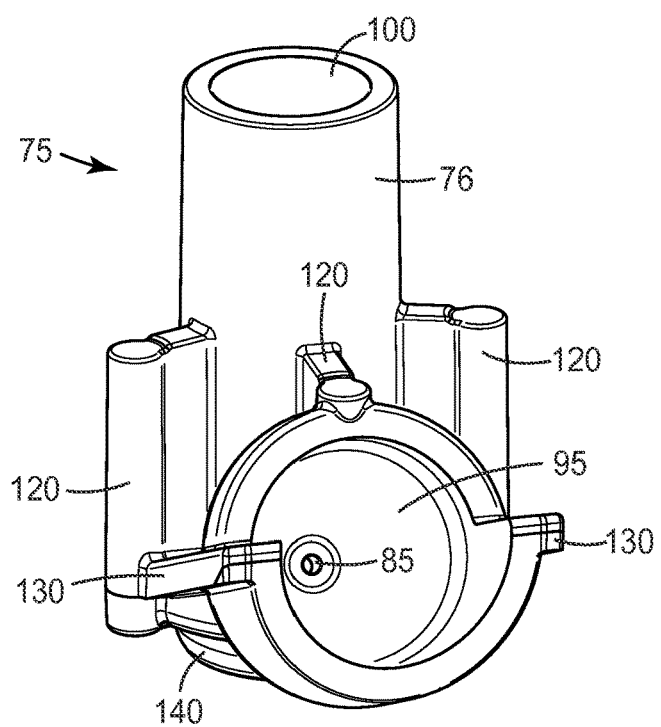
FIG. 9 is a perspective front view of the stem post of FIG. 8.
Figure 10:
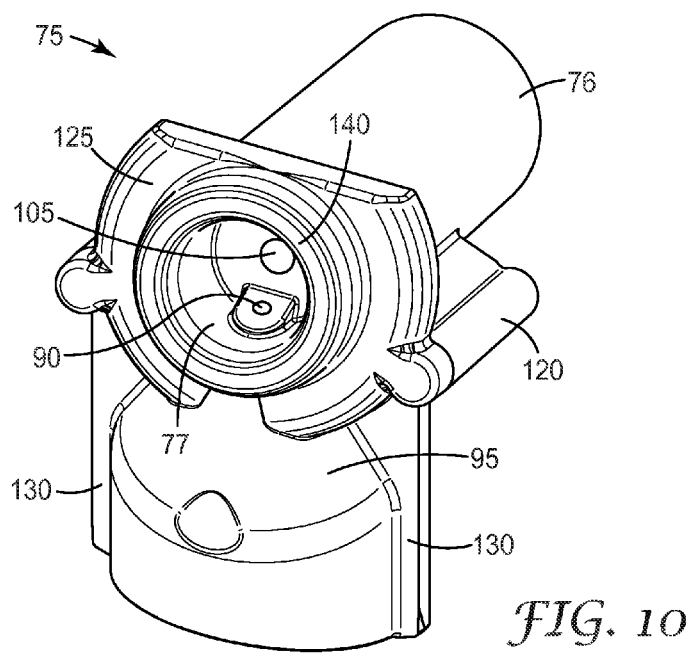
FIG. 10 is a perspective bottom view of the stem post of FIG. 8.

FIGS. 8, 9 and 10 show the stem post 75 with its stem socket 100 and stem ledge 110 (which contacts the canister metering valve 21 when a canister 20 is inserted in the actuator 10). The expansion chamber 105 receives medicament from the canister (not shown) and the expansion chamber 105 is in fluid communication with the transition region 77. The transition region 77 is open at the bottom but is sealed when the stem post 75 is in position in the actuator body 15. The transition region 77 is in fluid communication with the orifice outlet 85 and the jet portion 90 which in turn communicates with the stem post delivery passage 91 that is partially enclosed by the spray cone 95.

Figure 11:
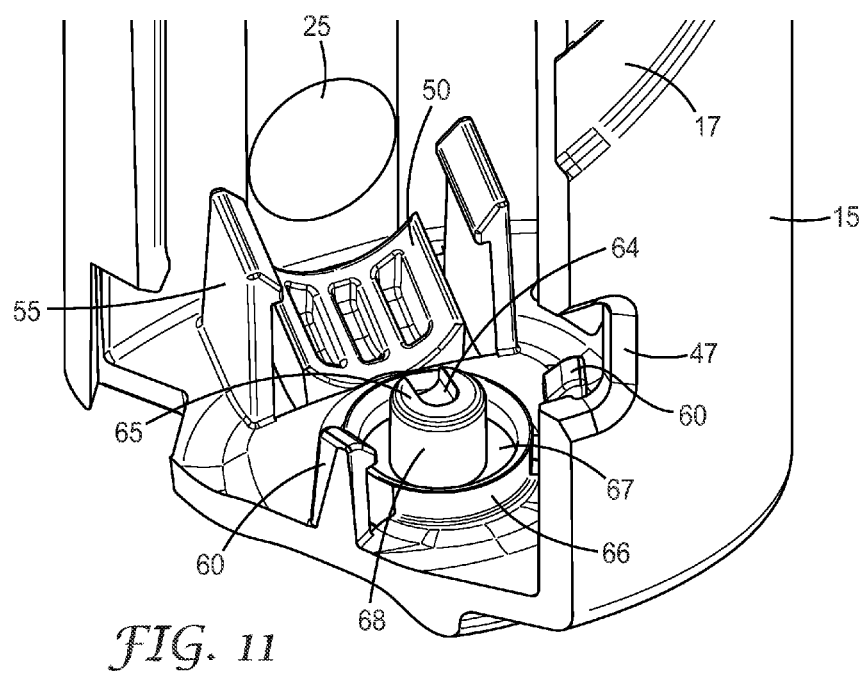
FIG. 11 is a partial rear perspective cut-away view of the body of the actuator of FIG. 4.

FIG. 11 shows a cut away view of the body 15 from the rear with the stem post 75 removed. The stem post delivery passage seat 50 supports the spray cone 95 of the stem post 75 when in use, and provides an alignment feature to ensure that the jet portion 90 of the orifice outlet 85 is aligned correctly with the delivery passage 25. The transition recess 64 in the post support 68 cooperates in use with the transition region 77 of the stem post 75 to form the transition chamber 70.

When the stem post 75 is inserted into the canister opening 11 of the actuator body, the press fit sealing ring 140 contacts the post support 68, with which it is a tight fit. Any interference between the parts and the radius at the edge of the post seat 65 cause the press fit sealing ring 140 to splay slightly. Upon further insertion, the press fit sealing ring 140 engages the lead-in portion at the inside top portion of the sealing rim 66. Any interference causes a return deformation of the press fit sealing ring 140, and provides a sealing engagement between the stem post 75 and the body 15 which prevents leakage of formulation or other formulation components that, in use, need to be contained within the transition chamber 70 to avoid any loss of dose. Preferably, the stem post is engaged such that the post seat 65 fits flush with the top of the transition region 77. Preferably the stem post 75 and/or the actuator body 15 is provided with alignment features to ensure that the orifice is correctly aligned with the delivery passage 25 to reduce deposition of spray on surfaces within the actuator 10.

It is to be understood that the specification is not limited to the embodiments described above and that various modifications can be made without departing from the principles or concepts of the specification. For example, the transition region of the stem post may in an alternative embodiment be flat or relatively small in volume and the transition recess of the actuator body may be relatively large. Alternatively, the body transition region may not be a transition recess but relatively flat or of low volume.

Actuators and inhalers according to the specification may include any feature described herein separately or in combination with any other feature(s), if necessary with appropriate modification of other features, as would be readily apparent to the skilled person.

The invention claimed is:

1. An inhaler for delivery of a medicament, the inhaler comprising an actuator and a canister, said canister comprising propellant and medicament, the actuator comprising
   a body, a stem post and fixing means for fixing the stem post in the body, wherein
   the body comprises a delivery passage for delivery of a medicament and a canister opening for insertion of a canister having a metering valve with a valve stem,
   the stem post comprises a stem socket for receiving the valve stem of a canister and comprises an orifice for discharging a medicament to the delivery passage, and wherein
   the stem post is adapted and the body is adapted so that the stem post and body cooperate to define a transition chamber when the stem post is fixed in the body, wherein the transition chamber is situated between the stem socket and the orifice.

2. The inhaler as claimed in claim 1, wherein the transition chamber is in fluid communication with the stem socket and the delivery passage.

3. The inhaler as claimed in claim 1, wherein the fixing means are adapted so that the stem post is fixable in the body by insertion of the stem post through the canister opening.

4. The inhaler as claimed in claim 1 wherein the stem post comprises a first transition region.

5. The inhaler as claimed in claim 4, wherein the first transition region is situated between the stem socket and the orifice.

6. The inhaler as claimed in claim 4, wherein the body comprises a second transition region.

7. The inhaler as claimed in claim 6, wherein the first transition region and the second transition region define the transition chamber when the stem post is fixed in the body.

8. The inhaler as claimed in claim 1, wherein the stem post further comprises an expansion chamber for receiving at least a portion of a metered dose of the medicament from the canister.

9. The inhaler as claimed in claim 8, wherein the expansion chamber is situated between the stem socket and the transition region.

10. The inhaler as claimed in claim 1, wherein the orifice has a jet portion of predetermined width and predetermined length.

11. The inhaler as claimed in claim 1 wherein the fixing means comprises at least one press fit seal.

12. The inhaler as claimed in claim 11, wherein at least one press fit seal comprises a ring and groove press fit seal.

13. The inhaler as claimed in claim 1, wherein the stem post is a unitary moulding.

14. The inhaler as claimed in claim 1, wherein the body is a unitary moulding.

15. The inhaler as claimed in claim 1, wherein the delivery passage comprises a nose piece adapted for nasal delivery of the medicament.

16. The inhaler as claimed in claim 1, wherein the body further comprises a window.

17. The inhaler as claimed in claim 1, further comprising supporting means for supporting a dose counter.

* * * * *